(12) United States Patent
Révész

(10) Patent No.: US 6,300,347 B1
(45) Date of Patent: Oct. 9, 2001

(54) 2-SUBSTITUTED 4,5-DIARYL IMIDAZOLES

(75) Inventor: László Révész, Therwil (CH)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 09/446,885

(22) PCT Filed: Jun. 26, 1998

(86) PCT No.: PCT/EP98/03930

§ 371 Date: Dec. 29, 1999

§ 102(e) Date: Dec. 29, 1999

(87) PCT Pub. No.: WO99/01449

PCT Pub. Date: Jan. 14, 1999

(30) Foreign Application Priority Data

Jun. 30, 1997 (GB) .................................. 9713726

(51) Int. Cl.⁷ .................... A61K 31/4439; C07D 401/14
(52) U.S. Cl. .................... 514/333; 514/202; 546/255; 546/256; 546/210; 546/193
(58) Field of Search .................... 546/184, 192, 546/193, 210, 255, 256; 514/202, 333

(56) References Cited

U.S. PATENT DOCUMENTS

| 5,717,100 | * | 2/1998 | Selnick et al. | 546/194 |
| 5,916,891 | | 6/1999 | Adams et al. | 514/256 |

FOREIGN PATENT DOCUMENTS

| 2772377 | 6/1999 | (FR) . |
| WO93/14081 | 7/1993 | (WO) . |
| WO93/14082 | 7/1993 | (WO) . |
| WO95/03297 | 2/1995 | (WO) . |
| WO96/03387 | 2/1996 | (WO) . |
| WO97/12876 | 4/1997 | (WO) . |
| WO98/47892 | 10/1998 | (WO) . |
| WO98/56788 | 12/1998 | (WO) . |
| WO98/57966 | 12/1998 | (WO) . |
| WO99/01130 | 1/1999 | (WO) . |
| WO99/01131 | 1/1999 | (WO) . |
| WO99/01136 | 1/1999 | (WO) . |
| WO99/01452 | 1/1999 | (WO) . |
| WO99/03837 | 1/1999 | (WO) . |

* cited by examiner

*Primary Examiner*—Alan L. Rotman
*Assistant Examiner*—Rita Desai
(74) *Attorney, Agent, or Firm*—Carol Loeschorn

(57) ABSTRACT

Novel 2-substituted 4,5-diaryl imidazoles are provided, in particular compounds of Formula I

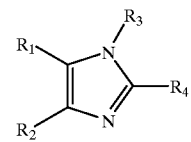

wherein R1, R2, R3 and R4 are as defined, in free or pharmaceutically-acceptable acid addition salt or physiologically-cleavable ester form, which have p38 MAP kinase (Mitogen Activated Protein Kinase) inhibiting activity. The compounds are used as pharmaceuticals for treating TNFα and IL-1 mediated diseases such as rheumatoid arthritis and diseases of bone metabolism, e.g. osteoporosis.

7 Claims, No Drawings

2-SUBSTITUTED 4,5-DIARYL IMIDAZOLES

This Application is a 371 of Application No. PCT/EP98/03930, filed Jun. 26, 1998.

This invention relates to 2-substituted 4,5-diaryl imidazoles and to their use for treatin TNFα and IL-1 mediated diseases such as rheumatoid arthritis and diseases of bone metabolism, e.g. osteoporosis.

Accordingly the present invention provides novel 2-substituted 4,5-diaryl imidazoles in which:

i) the nitrogen atom at the 1 position is substituted by a trialkylsilyl-containing substituent, or ii) the substituent at the 2 position is arylalkyl, arylsulfonyl, aryithio aryiseleno, aryltelluro, cycloalkyl, cycloalkenyl, alkylcycloalkyl, alkylcycloalkenyly, amino or hydrazino, or mono- or bicyclic N-heterocyclyl in which the N containing ring has six ring members, provided that the substituent at the 2 position is not piperidin-4-yl, 1-carboxylic-acid-tert-butyl-ester-4-benzyl-piperidin-4-yl, 1,4-dimethyl-piperidin-4-yl, 4-benzyl-piperidin-4-yl, or piperidinyl which is further substituted only at the N atom, and further provided that neither of the 4- or 5-aryl substituents is phenyl substituted with a radical selected from alkyisulfonyl or aminosulfonyl.

and pharmaceutically-acceptable acid addition salts thereof and physiologically-cleavable esters thereof.

The 4- or 5-aryl substituent may be any of those known in the art; for instance, as described in WO 95/03297 and WO 97/12876. For example, the 4- and 5-aryl substituents may be as hereinafter defined for $R_1$ and $R_2$ of formula I and include heteroaryl substituents.

When the nitrogen atom at the 1 position is substituted by a trialkylsiyl-containing substituent, the substituent is suitably a trialkylsilylalkoxyalkyl substituent.

When the substituent at the 2 position is arylalkyl, it is conveniently phenylalkyl.

When the substituent at the 2 position is arylalkyl, arylsulfonyl, arylthio arylseleno, aryltelluro, cycloalkyl, cycloalkenyl, alkylcycloalkyl, alkylcycloalkenyl, amino or hydrazino, or mono- or bicyclic N-heterocyclyl, it may be further substituted, e.g. by up to 6 substituents selected from halo, OH, $C_{1-4}$alkyl, $C_{2-4}$alkenyl, $C_{2-4}$alkynyl, $C_{1-4}$alkoxy, $C_{1-4}$ thioalkoxy, nitro, amino, $C_{1-4}$alkylsulphinyl, $C_{1-4}$ alkylsulphonyl, carboxylate or ester.

Above and elsewhere in the present description the terms halo or halogen denote I, Br, Cl or F, preferably F.

In particular embodiments the invention provides a compound of formula I

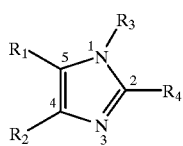

I wherein
$R_1$ is 4-pyridyl, pyrimidinyl, quinazolin-4-yl, quinolyl, isoquinolyl, 1-imidazolyl or 1-benzamidazolyl, which is optionally substituted with one or two substituents each of which is independently selected from $C_{1-4}$alkyl, halogen, $C_{1-4}$alkoxy, $C_{1-4}$alkylthio, $NR_5R_6$, or an N-heterocyclyl ring having 5 to 7 ring atoms and optionally containing an additional heteroatom selected from O, S, or N wherein $R_5$ and $R_6$ is each independently $C_{1-4}$alkyl;
$R_2$ is phenyl, naphth-1-yl or naphth-2-yl which is optionally substituted by up to 5 substituents;
$R_3$ is hydrogen,
  heterocyclyl,
  heterocyclyl$C_{1-10}$alkyl,
  tri$C_{1-4}$alkylsilyl$C_{1-10}$alkoxy$C_{1-4}$alkyl,
  optionally halo substituted $C_{1-10}$alkyl, $C_{2-10}$ alkenyl, $C_{2-10}$ alkynyl, $C_{3-7}$ cycloalkyl, $C_{3-7}$ cycloalkyl$C_{1-10}$ alkyl, $C_{5-7}$ cycloalkenyl, aryl, aryl$C_{1-10}$alkyl, heteroaryl, or heteroaryl$C_{1-10}$alkyl,
  optionally mono- or di-$C_{1-4}$alkyl-substituted$C_{0-10}$alkyl-oxycarbonyl or -oxythiocarbonyl optionally substituted by $C_{1-10}$alkyl, $C_{3-7}$ cycloalkyl, heterocyclyl, heterocyclyl$C_{1-10}$alkyl, aryl, aryl$C_{1-10}$alkyl, heteroaryl, heteroaryl$C_{1-10}$alkyl, or
  mono- or di-$C_{1-4}$alkyl-substituted$C_{1-10}$alkyl optionally substituted by
    cyano,
    nitro,
    hydroxy, $C_{1-10}$alkoxy, $C_{3-7}$cycloalkoxy, heterocycloxy,
    heterocyclyl$C_{1-10}$alkoxy, aryloxy, aryl$C_{1-10}$alkoxy, heteroaryloxy,
    heteroaryl$C_{1-10}$alkoxy,
    optionally substituted amino, carboxylate, thiocarboxylate,
    carbonyl or thiocarbonyl, sulphinyl or suiphonyl,
$R_4$ is mono- or di-$C_{3-7}$cycloalkyl-$C_{0-4}$alkyl optionally substituted by -halo, —OH, —$C_{1-4}$ alky, —$C_{1-4}$ alkoxy, —$C_{1-4}$ thioalkoxy, -nitro, -amino, —$C_{1-4}$ alkylsulphinyl, —$C_{1-4}$ alkylsulphonyl, -carboxylate or -ester,
  —$NR_7R_8$, $NHNHR_9$,
  wherein independently each $R_7$, $R_8$ or $R_9$, is $C_{1-4}$alkyl, $C_{2-4}$alkenyl, $C_{2-6}$alkynyl,
  —X—$C_{5-10}$ aryl (including heteroaryl)
  wherein X is S, $SO_2$, Se, Te or $C_{1-4}$alkyl,
  mono- or bicyclic N-heterocyclyl in which the N containing ring has six ring members,
  or aryl or heteroaryl optionally substituted by up to 4 substituents, provided that
when $R_3$ is not tri$C_{1-4}$alkylsilyl$C_{1-10}$alkoxy$C_{1-4}$alkyl,
$R_4$ is not aryl or heteroaryl optionally substituted by up to 3 substituents, except when $R_4$ is mono- or bicyclic N-heterocyclyl in which the N containing ring has six ring members,
further provided that
$R_4$ is not piperidin-4-yl, 1-carboxylic-acid-tert-butyl-ester-4-benzyl-piperidin-4-yl, 1,4-dimethyl-piperidin-4-yl, 4-benzyl-piperidin-4-yl, or piperidinyl which is further substituted only at the N atom, and
yet further provided that $R_2$ is not phenyl substituted with a radical selected from alkylsulfonyl or aminosulfonyl,
and pharmaceutically-acceptable acid addition salts thereof and physiologically-cleavable esters thereof.

$R_2$ is substituted by up to 5 substituents which may be any of the substituents known in the art; for instance, as described for $R_4$ in WO 95/03297 and the substituent R of WO 97/12876.

When $R_4$ is —X—$C_{5-10}$aryl, the $C_{5-10}$aryl or X, when it is $C_{1-4}$alkyl, may be substituted by up to 6 substituents selected from halo, OH, $C_{1-4}$ alkyl, $C_{1-4}$ alkoxy, $C_{1-4}$ thioalkoxy, nitro, amino, $C_{1-4}$ alkylsulphinyl, $C_{1-4}$ alkylsulphonyl, carboxylate or ester.

When $R_4$ is mono- or bicyclic N,-heterocyclyl in which the N containing ring has six ring members, it may be saturated or unsaturated, e.g. aromatic, heterocyclyl.

When $R_4$ is aryl or heteroaryl optionally substituted by up to 4 substituents, $R_4$ may comprise one of the customary aryl or heteroaryl substituents used in the art; for instance as defined for the substituent $R_3$ of WO 93/03297.

Imidazoles with a 2-substituent, e.g. $R_4$ as defined above, and with also aryl substituents at both positions 4 and 5, e.g. as defined for $R_1$ and $R_2$ above, in which the nitrogen atom at the 1 position is substituted by a trialkylsilyl-containing substituent are entirely novel.

Accordingly in a further aspect the invention provides a compound of formula I'

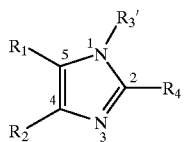

I' wherein $R_3'$ is $triC_{1-4}alkylsilylC_{1-10}alkoxyC_{1-4}alkyl$, and $R_1$, $R_2$ and $R_4$ are as defined above, and pharmaceutically-acceptable acid addition salts thereof and physiologically-cleavable esters thereof.

Compounds of formula I' in which $R_4$ is H and $R_2$, $R_3'$ and $R_4$ as defined above are key intermediates for the synthesis of other compounds of formula I in which $R_3$ is not $triC_{1-4}alkylsilylC_{1-10}alkoxyC_{1-4}alkyl$, as hereinafter described.

The substituents $R_1$, $R_2$, $R_3$, $R_3'$ and $R_4'$ independently have the following preferred significances.

Preferably $R_1$ is 4-pyridyl or pyrimidinyl, especially 4-pyridyl.

$R_2$ is preferably phenyl, including substituted phenyl.

Most preferably $R_3'$ is trimethylsilylethoxymethyl.

When $R_3$ is $triC_{1-4}alkylsilylC_{1-10}alkoxyC_{1-4}alkyl$, $R_1$ is preferably 4-pyridyl.

When $R_3$ is $triC_{1-4}alkylsilylC_{1-10}alkoxyC_{1-4}alkyl$, $R_2$ is preferably 4-fluorophenyl.

When $R_3$ is $triC_{1-4}alkylsilylC_{1-10}alkoxyC_{1-4}alkyl$, $R_4$ is preferably H.

In a further preferred aspect of the invention $R_4$ is —X—$C_{5-10}$aryl, preferably —X—phenyl, wherein X is as previously defined, e.g. a compound of formula III

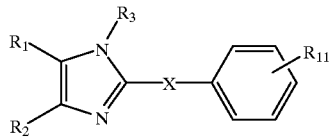

III wherein $R_1$, $R_2$, $R_3$ and X are as defined above and $R_{11}$ represent from 1–4, substituents independently selected from H, halo, OH, $C_{1-4}$ alkyl, $C_{1-4}$ alkoxy, $C_{1-4}$ thioalkoxy, nitro, amino, $C_{1-4}$ alkylsulphinyl, $C_{1-4}$ alkylsulphonyl, carboxylate or ester, and pharmaceutically-acceptable acid addition salts thereof and physiologically-cleavable esters thereof.

In a yet further preferred aspect of the invention $R_4$ is cycloalkyl, cycloalkenyl, alkylcycloalkyl, alkylcycloalkenyl, or mono- or bicxclic N-heterocyclyl in which the N containing rinng has six ring members, e.g. a compound of formula IV

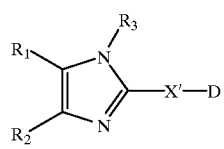

IV wherein $R_1$, $R_2$ and $R_3$ are as defined above, D is $C_{3-7}$cycloalkyl, $C_{3-7}$cycloalkenyl or a mono- or bicyclic N-heterocyclyl in which the N containing ring has 6 ring members and X' is a direct bond or —$CR_{12}R_{13}$— wherein $R_{12}$ is H or $C_{1-4}$alkyl and $R_{13}$ is H or $C_{1-4}$alkyl optionally substituted by $C_{3-7}$cycloalkyl or $C_{3-7}$cycloalkenyl, with the proviso that X' is a direct bond when D is a mono- or bicyclic N-heterocyclyl in which the N containing ring has 6 ring members, and pharmaceutically-acceptable acid addition salts thereof and physiologically-cleavable esters thereof.

In formula IV X' and D may be further substituted, e.g. by up to 6 substituents selected from halo, OH, $C_{1-4}$ alkyl, $C_{1-6}$ alkoxy, $C_{1-4}$ thioalkoxy, nitro, amino, $C_{1-4}$ alkylsulphinyl, $C_{1-4}$ alkylsulphonyl, carboxylate or ester.

Preferably D is cyclohexyl, cyclohexenyl, cyclopropyl, pyridinyl (e.g. 4-pyridinyl), piperidinyl (e.g. piperidin-4-yl), piperidenyl (e.g. piperiden-4-yl), azabicyclo[3,2,1]octanyl, azabicyclo[3,3,1]nonyl or tropanyl bicyclic N-heterocycles (and enyl anologues of such bicyclic N-heterocycles, e.g. 8-azabicyclo{3.2.1}oct-2-en-3-yl). In particularly preferred embodiments —X'—D is 1-hydroxycyclohexyl, 1-aminocyclohexyl, 1-cyclohexenyl, cyclopropylmethyl, 1,2-dicyclopropylethyl, 2,3,5,6-tetrafluoropyridinyl, 2-amino-3,5,6-trifluoropyridinyl, 2,6-diamino-3,5-difluoropyridinyl, tropan-3-olyl, 4-hydroxy-1-methylpiperidinyl, 4-$C_{1-6}$alkoxy-1-methylpiperidinyl, e.g. 4-n-butyloxy-1-methylpiperidinyl, 8-methyl-8-azabicyclo{3.2.1}oct-2-en-3-yl), 1-methyl-4-piperidinyl.

When $R_4$ is —X—aryl or —X'—D, $R_1$ is preferably 4-pyridyl.

When $R_4$ is —X—aryl or —X'—D, $R_2$ is preferably halo substituted phenyl, especially 4-tluoro-phenyl.

When $R_4$ is —X—aryl or —X'—D, $R_3$ is preferably H.

Particularly preferred compounds of formula IV are those in which X' is a direct bond and D is optionally substituted pyridinyl, e.g. 4-pyridinyl, or piperidinyl, e.g. piperidin-4-yl.

The novel 2-substituted 4,5-diaryl imidazoles of the invention, in particular the compounds of formulae I to IV and the specific compounds of Examples 1–19 are hereinafter referred to as "Compounds of the Invention".

The Compounds of the Invention which comprise free hydroxyl groups may also exist in the form of pharmaceutically acceptable, physiologically cleavable esters, and as such are included within the scope of the invention. Such pharmaceutically acceptable esters are preferably prodrug ester derivatives, such being convertible by solvolysis or cleavage under physiological conditions to the corresponding Compounds of the Invention which comprise free hydroxyl groups. Suitable pharmaceutically acceptable prodrug esters are those derived from a carboxylic acid, a carbonic acid monoester or a carbamic acid, advantageously esters derived from an optionally substituted lower alkanoic acid or an arylcarboxylic acid.

The Compounds of the Invention may also exist in the form of pharmaceutically acceptable salts, and as such are included within the scope of the invention. Pharmaceutically acceptable salts include acid addition salts with conventional acids, for example, mineral acids, e.g., hydrochloric acid, sulfuric or phosphoric acid, or organic acids, for example, aliphatic or aromatic carboxylic or sulfonic acids, e.g., acetic, propionic, succinic, glycolic, lactic, malic, tartaric, citric, ascorbic, maleic, fumaric, hydroxymaleic, pyruvic, pamoic, methanesulfonic, toluenesulfonic, naphthalenesulfonic. sulfanilic or cyclohexylsulfamic acid, also amino acids, such as arginine and lysine. For compounds of the invention having acidic groups, for example, a free carboxy group, pharmaceutically acceptable salts also represent metal or ammonium salts, such as alkali metal or alkaline earth metal salts, e.g., sodium potassium, magnesium or calcium salts, as well as ammonium salts, which are formed with ammonia or suitable organic amines.

Compounds of the Invention of formulae III and IV as defined above may be prepared by reacting a compound of formula VIII

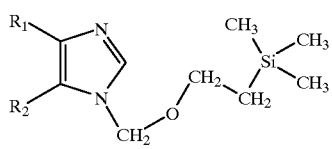

VIII wherein $R_1$ and $R_2$ are as defined above, with the corresponding aldehyde, ketone, disulfonylamine, disulfide, diselenide, ditelluride or halide and, if required introducing the desired $R_3$ substituent or further transforming the product obtained and optionally recovering it free or salt form. Thus for example, the compound of formula VIII is treated with the corresponding aldehyde, ketone, disulfonylamine, disulfide, diselenide, ditelluride or halide in the presence of n-BuLi, e.g. in cooled (e.g. −40° C.) THF solution.

When the compound of formula VIII is treated with the corresponding aldehyde or ketone, the initial product obtained is 1-hydroxy substituted in the $R_4$ substituent, e.g. 1-hydroxycyclohexyl when the ketone is cyclohexanone. The corresponding dehydrated compound. e.g. $R_4$ is 1-cyclohexenyl, may be obtained, e.g. by treatment with pTsOH under reflux in toluene solution.

The invention includes a process for the preparation of a Compound of the Invention or salt of formulae III and IV as defined above which comprises reacting a compound of formula VIII

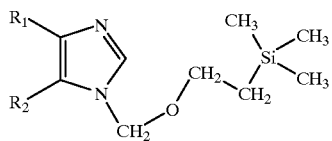

VIII wherein $R_1$ and $R_2$ are as defined above, with the corresponding aldehyde, ketone, disulfonylamine, disulfide, diselenide, ditelluride or halide and, if required introducing the desired $R_3$ substituent or further transforming the product obtained and optionally recovering the Compound of the Invention in free or salt form.

Compounds of formula VIII may be prepared by treating the corresponding 1H-imidazole of formula I, i.e. the corresponding compound of formula I in which $R_4$ is H, with 2(trimethylsilyl)ethoxymethyl-halide (e.g. -chloride), e.g. in the presence of potassium bis-(trimethylsilyl)-amide in cooled (e.g. −78° C.) DMF/THF solution. This procedure gives rise to a mixture of the corresponding 1-2 (trimethylsilyl)-ethoxymethyl-imidazoles of formulae VIII and IX

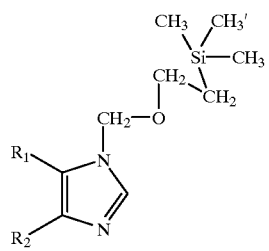

IX wherein $R_1$ and $R_2$ are as defined above.

Compounds of formula VIII are novel intermediates for preparation of other Compounds of the Invention and are included per se within the present invention. Compounds of formula IX are Compounds of the Invention.

In an alternative preferred embodiment an alkoxyalkyl nitorogen protecting group, e.g. a dialkoxyalkyl nitrogen protecting group, especially a diethoxymethyl protecting group, is uswed in place of the trimethylsilylethoxymethyl protecting group. Such an alkoxyalkyl protecting group may be introduced by treating the corresponding 1H-imidazole of formula I, i.e. the corresponding compound of formula I in which $R_4$ is H, with a trialkyl orthoformate, e.g. triethyl orthoformate, for instance as hereinafter described in Example.

The synthesis of Compounds of the Invention is further described in the following Examples.

EXAMPLES

Example 1 and 2

4-(4-fluorophenyl)-5-(4-pyridyl)-1-(2-(trimethylsilyl)-ethoxymethyl)-imidazole and 4-(4-pyridyl)-5-(4-fluorophenyl)-1-(2-(trimethylsilyl) ethoxymethyl)imidazole

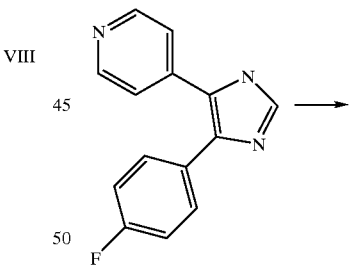

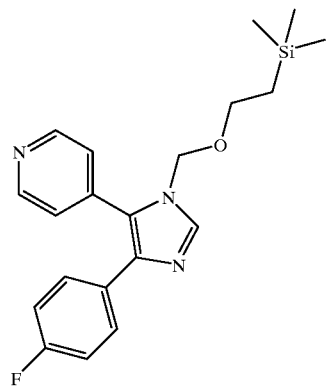

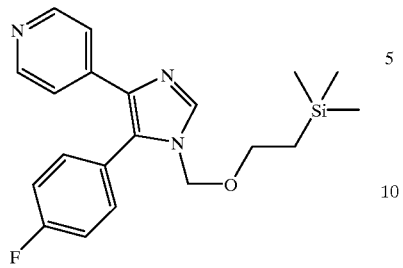

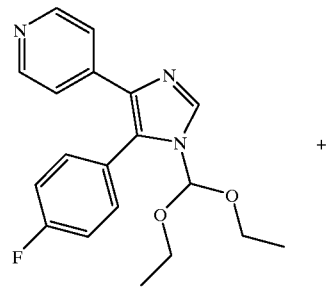

4-(4-Fluorophenyl)-5-(4-pyridyl)-1H-imidazole (3) (1 g 4.18 mmol) is dissolved in DMF/THF (50 ml/20 ml) and cooled to −78° C. Potassium bis-(trimethylsilyl)-amide (15% in toluene; 6.7 ml 5 mmol) is introduced at −78° C., stirred for 30 min. then 2-(trimethylsilyl) ethoxymethylchloride is added and the reaction mixture warmed up to r.t., poured on water after 2 hrs. and extracted 3× with ethyl acetate. The combined organic phases are dried over $Na_2SO_4$, evaporated to dryness and chromatographed ($SiO_2$ acetone/hexane 4/6 to 6/4) to give 1-(2-(trimethylsilyl)ethoxymethyl)-4-(4-fluorophenyl)-5-(4-pyridyl)imidazole, being eluted first as white crystals (218 mg 14%) followed by 4-(4-pyridyl)-5-(4-fluorophenyl)-1-(2-(trimethylsilyl)ethoxymethyl) imidazole as white crystals (590 mg 38%). The correct assignment of the structures was achieved by ROESY, HSQC and HMBC spectrometry.

1H-NMR (360 MHz CDCl3) of 1-(2-(trimethylsilyl) ethoxymethyl)-4-(4-fluorophenyl)-5-(4-pyridyl)imidazole (Example 1): 0.00 (s, 9H); 0.92 (t, 2H); 3.55 (t, 2H); 5.15 (s, 2H); 6.95 (t, 2H); 7.36 (d, 2H); 7.42 (dd, 2H); 7.72 (s, 1H); 8.68 (d, 2H) 4-(4-pyridyl)-5-(4-fluorophenyl)-1-(2-(trimethylsilyl)ethoxymethyl)imidazole (Example 2): 0.00 (s, 9H); 0.90 (t, 2H); 3.48 (t, 2H); 5.10 (s, 2H); 7.20 (t, 2H); 7.35–7.45 (m, 4H); 7.75 (s, 1H); 8.45 (d, 2H).

Alternatively, the 1H-imidazole starting material may be converted to the corresponding 4-(4-fluorophenyl)-5-(4-pyridyl)-1-(1,1-diethoxymethyl)-imidazole and 4-(4-pyridyl)-5-(4-fluorophenyl)-1-(1,1-diethoxymethyl) imidazole products.

1-(1,1-Diethoxymethyl)-4-(4-fluorophenyl)-5-(4-pyridinyl)imidazole and 1-(1,1-diethoxymethyl-5-(4-fluorophenyl)-4-(4-pyridinyl)imidazole

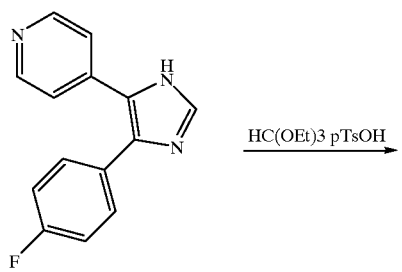

HC(OEt)3 pTsOH 4-(4-fluorophenyl)-5-(4-pyridinyl)-imidazole (72.7 g; 0.304 mol) and pTsOH.H₂O (1,1g; 5 mmol) are dissolved in hot triethyl orthoformate (770 ml) and refluxed, while slowly distilling off ca. 300 ml of triethyl orthoformate and ethanol. After 2 h the reaction mixture is evaporated to dryness and taken up in tert.butyl methyl ether (500 ml). Hexane (5 l) is slowly added, the precipitate filtered off and washed with tert.butyl methyl ether/hexane (1:9). The filtrate is washed with 1N $Na_2CO_3$, dried over $Na_2SO_4$ and evaporated. Xylene is added twice and evaporated again yielding the title compounds as a yellow-brownish viscuous oil (79.3 g; 76%, ~1:1 mixture), which is used without further purification.

Example 3

4-(4-fluorophenyl)-2-((RS)-1-hydroxy-4'-fluorobenzyl)-5-(4-pyridyl)imidazole

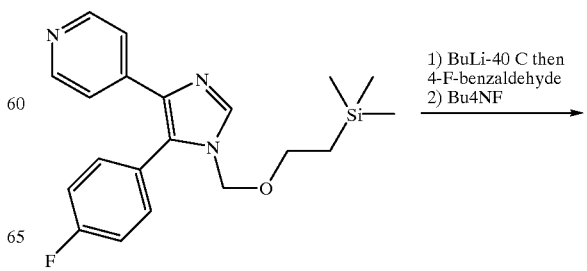

1) BuLi-40 C then 4-F-benzaldehyde
2) Bu4NF

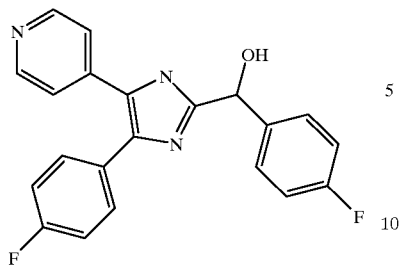

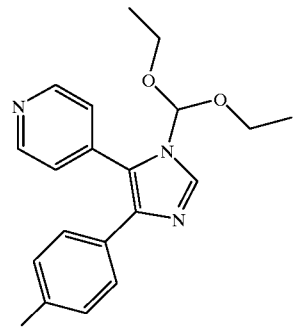

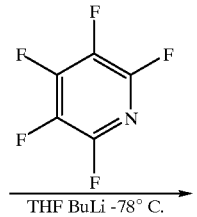

1.6M n-BuLi in hexane (0.085 ml 0.13 mmol) is added at −40° C. to a solution of 1-(2-(trimethylsilyl)ethoxymethyl)-4-(4-fluorophenyl)-5-(4-pyridyl)imidazole (Example 2; 50 mg 0.13 mmol) in THF (1.4 ml). After 15 min at −40° C. 4-fluorobenzaldehyde (0.018 ml 0.18 mmol) in THF (0.4 ml) is addded to the reaction mixture, which is warmed to r.t. and after 10 min. poured on water and extracted 3× with ethyl acetate. The combined organic phases are dried over $Na_2SO_4$, evaporated to dryness and render the desired is-protected title compound (64 mg). In order to remove the SEM protecting group, the latter material is dissolved in THF (2 ml), treated with Bu4NF (4.3 ml; 1M in THF) for 1 h at 60° C., poured on a saturated solution of $NaHCO_3$ and extracted 3× with ethyl acetate. The combined organic phases are dried over $Na_2SO_4$, evaporated to dryness and chromatographed ($SiO_2$ toluene/EtOH/$NH_3$conc. 90/10/0.6) to yield the title compound as white crystals (32 mg 67% over 2 steps)

1H-NMR (360 MHz DMSO-d6): 5.80 (s, 1H); 6.30 (bs, OH); 7.15 (t, 2H); 7.20–7.30 (bs, 1H); 7.37 (d, 2H); 7.42–7.48 (m, 2H); 7.52–7.58 (m, 2H); 8.38–8.51 (bs, 2H); 12.50–12.60 (bs, NH).

In an alternative procedure a mixture of 1-(1,1-diethoxymethyl)-4-(4-fluorophenyl)-5-(4-pyridinyl)imidazole and 3-(1,1-diethoxymethyl)-4-(4-fluorophenyl)-5-(4-pyridinyl)imidazole, prepared as described above may be used in place of 1-(2-(trimethylsilyl)ethoxymethyl)-4-(4-fluorophenyl)-5-(4-pyrldyl)imidazole; for example as described below for the preparation of 4-(4-Fluorophenyl)-5-(4-pyridyl) 2-(2,3,5,6-tetrafluoropyridinyl)imidazole.

4-(4-Fluorophenyl)-5-(4-pyridyl) 2-(2,3,5,6-tetrafluoropyridinyl)imidazole

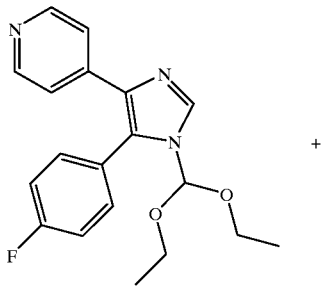

+

1.6 M nBuLi (66 ml; 45 mmol) is added at −45° C. to a ~1:1 mixture of 1-(1,1-diethoxymethyl)-4-(4-fluorophenyl)-5-(4-pyridinyl)imidazole and 1-(1,1-diethoxymethyl)-5-(4-fluorophenyl)-4-(4-pyridinyl)imidazole (15 g; 43 mmol) in THF (210 ml). After 15 min. at −45° C. the reaction mixture is cooled to −55° C. and pentafluoropyridine (5.1 ml; 47 mmol) is rapidly introduced. The cooling bath is removed, the reaction mixture allowed to warm to −15° C. and poured on water (1 l), which is then acidified with 2N HCl (100 ml). After stirring for 5 min. the mixture is combined with a saturated solution of $Na_2CO_3$ and extracted with ethyl acetate three times. The combined organic phases are dried over $Na_2SO_4$, filtered and evaporated to dryness rendering the title compound as brownish crystals (16.3 g). Chromatography ($SiO_2$; acetone/hexanes 1:1) yields the title compound together with some unreacted and unprotected imidazole starting material, which could be removed by washing with acetone yielding the title compound (8.7 g; 52.4%).

1H-NMR (360 Mhz CDCl3): 7.30–7.40 (bt, 2H); 7.45 (d, 2H); 7.58 (bq; 2H); 8.52 (bs, 2H). MS (m/z): 388.9 (MH+).

Using substantially similar procedures to those described in Example 3 and appropriate starting materials the following compounds of formula X are prepared as set out in Table I.

X

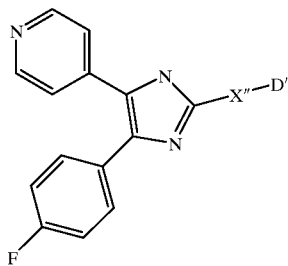

TABLE 1

| Example No. | X" | D' | NMR data etc. |
|---|---|---|---|
| 4 | —SO$_2$— | 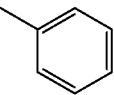 | 1H-NMR(360MHz DMSO-d6): 7.28(t, 2H); 7.35(d, 2H); 7.49(m, 2H); 7.67–7.80 (m, 3H); 8.05(d, 2H); 8.50(d, 2H) |
| 5 | —S— | 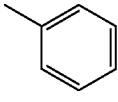 | 1H-NMR(360MHz DMSO-d6): 7.20–7.45 (m, 9H); 7.55(dd, 2H); 8.40–8.60(m, 2H) |
| 6 | —Se— | 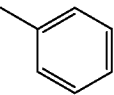 | 1H-NMR(360MHz DMSO-d6): 7.25–7.36 (5H); 7.40(d, 2H); 7.48–7.55(m, 4H); 8.48 (d, 2H) |
| 7 | direct bond | 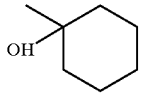 | 1H-NMR(360MHz DMSO-d6). 7/3 mixture of NH-tautomers: 1.20–1.40(bs, 1H); 1.51 (bs, 3H); 1.60–1.72(m, 2H); 1.72–1.85(m, 2H); 1.90–2.05(M, 2H); 5.60(s, 0.7H); 5.67 (s, 0.3H); 7.12–7.21 (bt, 0.3H); 7.30 (bt, 0.7H); 7.40(d, 2H); 7.48(bt, 2H); 8.40(bd, 1.4H); 8.48(bd, 0.6H); 12.26(s, 1H) |
| 8 | direct bond | 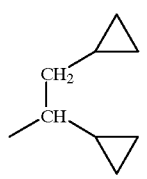 | 1H–NMR(360Mhz DMSO-d6): 0.00(bs, 1H); 0.20–0.30(m, 2H); 0.32–0.43(m, 2H); 0.50–0.60(m, 1H); 0.65–0.75(m, 1H); 1.05–1.15(m, 1H); 1.60–1.70(m, 1H); 1.81–1.91 (m, 1H); 2.10–2.20(m, 1H); 7.15–7.40(m, 4H); 7.50(dd, 2H); 8.4(bs, 1H); 8.45(bs, 1H); 12.20(bs, 1H) MS(m/z): 348(MH+) |
| 9 | —CH$_2$— |  | 1H-NMR (360Mhz CDCl$_3$): 0.48(q, 2H); 0.68(q, 2H); 1.20(m, 1H); 2.84(d, 2H); 7.10 (t, 2H); 7.45(dd, 2H); 7.55(d, 2H); 8.45(d, 2H) MS(m/z):294(MH+) |
| 10 | direct bond | 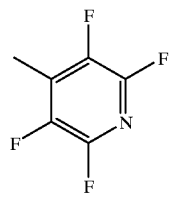 | 1H-NMR(360Mhz CDCl3): 7.30–7.40 (bt, 2H); 7.45(d, 2H); 7.58(bq; 2H); 8.52 (bs, 2H). MS (m/z): 388.9(MH+) |
| 11 | direct bond | 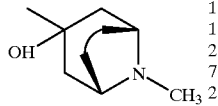 | 1H-NMR(360Mhz DMSO): 1.83(bd; 2H); 1.90(bs, 2H); 2.13(bd, 2H); 2.25(bs, 2H); 2.40(bd, 2H); 3.12(bs, 3H); 5.15(bs, 1H); 7.20–7.30(bs, 2H); 7.46(d, 2H); 7.45(dd, 2H); 8.35–8.50(s, 2H); 12.25(s, 1H). MS(m/z): 377.1(MH−) |
| 12 | direct bond | 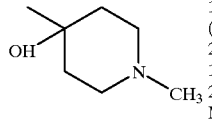 | 1H-NMR(360Mhz DMSO, 120 C): 2.18 (bt; 1H); 2.21(bt; 1H); 2.40–2.50(m, 2H); 2.78 (s, 3H); 2.7–2.95(bm, 4H); 5.45(bs, 1H); 7.21(dd, 2H); 7.42(dd, 2H); 7.51(dd, 2H); 8.45(dd, 2H). MS(m/z): 352(M+) |

Example 13

2-(1-Cyclohexenyl)-4-(4-fluorophenyl)-5-(4-pyridyl) imidazole

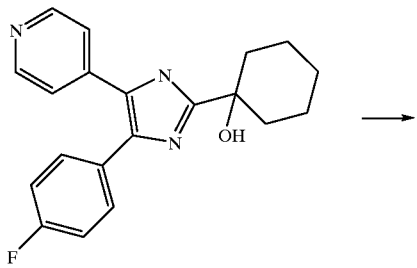

→

The product of Example 7, 2-((1-hydroxy)cyclohexyl)-4-(4-fluorophenyl)-5-(4-pyridyl)-1H-imidazole (50 mg 0.15 mmol) is dissolved in toulene (100 ml) and refluxed with pTsOH (100 mg) for 15 min. The reaction mixture is poured on saturated $NaHCO_3$ and extracted 3× with ethyl acetate. The combined organic phases are dried over $Na_2SO_4$, evaporated to dryness and chromatographed ($SiO_2$ acetone/hexane 4/6) to render the title compound as white crystals (38 mg 81%), 1H-NMR (360 MHz DMSO-d6), 8/2 mixture of NH-tautomers: 1.60 (m, 2H); 1.68 (m, 2H); 2.18 (bs, 2H); 2.50 (bs, 2H); 6.55 (bs 0.8H); 6.62 (bs, 0.2H); 7.15–7.60 (m, 6H); 8.40 (d, 1.6H); 8.52 (d, 0.4H); 12.25 (bs, 0.2H); 12.37 (bs, 0.8H).

Using substantially similar procedures to those described in Example 13 and appropriate starting materials the following compounds of formula X are prepared as set out in Table 2.

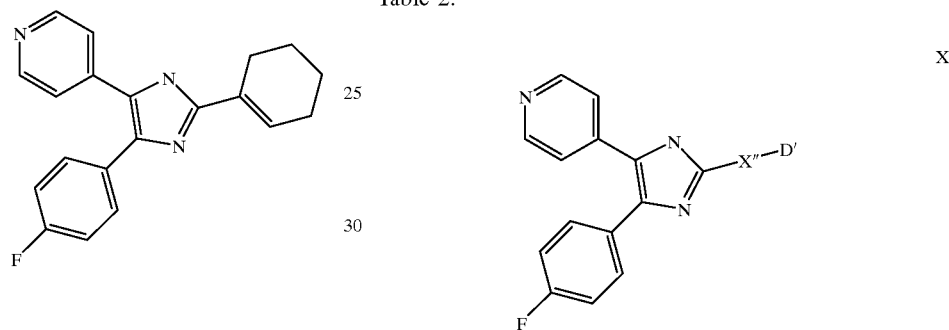

X

TABLE 2

| Example No. | X" | D' | NMR data etc. |
|---|---|---|---|
| 14 | direct bond | (4-methyl-tropane-N-CH₃) | 1H-NMR(360Mhz DMSO, 120 C): 1.55–1.65 (m, 2H); 1.72(dt, 2H), 2.00–2.18(m, 2H); 2.22 (d, 1H); 2.35(s, 3H); 3.35(bt, 1H); 3.42(bt, 1H); 6.68(bs, 1H); 7.10–7.30(bd, 2H); 7.40(d, 2H), 7.50(dd, 2H); 8.35–8.55(bd, 2H); 12.00(bs, 1H). MS(m/z): 361.1(M+H+). |
| 15₁ | direct bond | (4-methyl-tetrahydropyridine-N-CH₃) | 1H-NMR(360MHz, DMSO, 120 C): 2.35(s, 3H): 2.65(s, 4H); 3.10(s, 2H); 6.55(bs, 1H); 7.10–7.30(bd, 2H); 7.42(bs, 2H); 7.52(bt, 2H); 8.35–8.55(bd, 2H); 11.90–12.10(bs, 1H). MS(m/z): 334(M+). |

₁SOCl₂ in pyridine is used in place of pTsOH in toluene

Example 16 and 17

4-(4-Fluorophenyl)-5-(4-pyridyl) 2-(2-amino-3,5,6-trifluoropyridinyl)imidazole and 4-(4-Fluorophenyl)-5-(4-pyridyl) 2-(2,6-diamino-3,5-difluoropyridinyl)imidazole

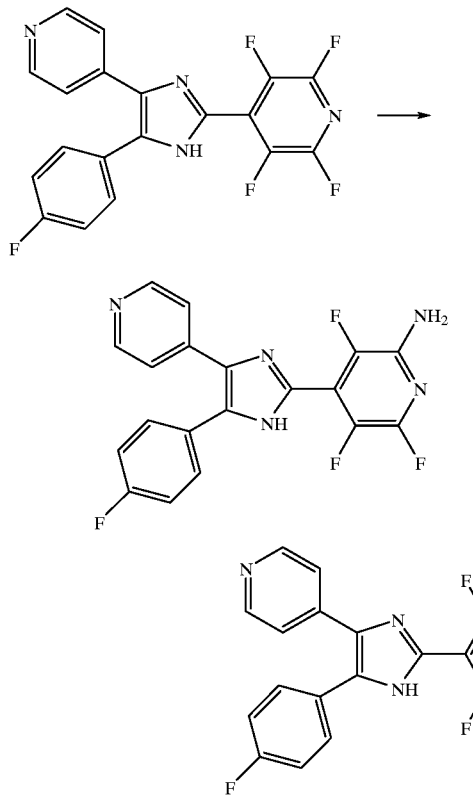

The product of Example 10, 4-(4-Fluorophenyl)-5-(4-pyridyl) 2-(2,3,5,6-tetrafluoropyridinyl)imidazole (2 g; 5.15 mmol) is suspended in NH₃conc. (25%; 200 ml) and heated to 150° C. in a sealed steal cylinder for 5 h. Water is evaporated and the residue chromatographed (SiO₂, TBME/MeOH/NH₃ conc 98/2/0.2) to yield the title compounds 4-(4-Fluorophenyl)-5-(4-pyridyl) 2-(2-amino-3,5,6-trifluoropyridinyl)imidazole (880 mg; 44.4%) and 4-(4-Fluorophenyl)-5-(4-pyridyl) 2-(2,6-diamino-3,5-difluoropyridinyl)imidazole (650 mg; 33%) as slightly colored crystals.

4-(4-Fluorophenyl)-5-(4-pyridyl) 2-(2-amino-3,5,6-trifluoropyridinyl)imidazole 1H-NMR (400 MHz, DMSO-d6) mixture of tautomers: 6.80 (s, 2H); 7.25 (bt, 0.6H); 7.38 (t, 1.4H); 7.45 (d, 2H); 7.58 (t, 2H); 8.49 (d, 1.4H): 8.62 (bd, 0.6H) MS (m/z): 385 (M+) 4-(4-Fluorophenyl)-5-(4-pyridyl) 2-(2,6-diamino-3,5-difluoropyridinyl) imidazole: 1H-NMR (400 MHz, DMSO-d6) mixture of tautomers: 5.75 (s, 2H); 7.22 (t, 0.6H); 7.33 (t, 1.4H); 7.41–7.47 (m, 2H); 7.52–7.58 (m, 2H); 8.47 (d, 1.4H); 8.58 (d, 0.6H) MS (m/z): 382 (M+).

Example 18

4-(4-Fluorophenyl)-2-((1-amino)cyclohexyl)-5-(4-pyridyl)imidazole a) 1-(4-Fluorophenyl)-2-bromo-2-(4-pyridyl)ethanone hydrobromide

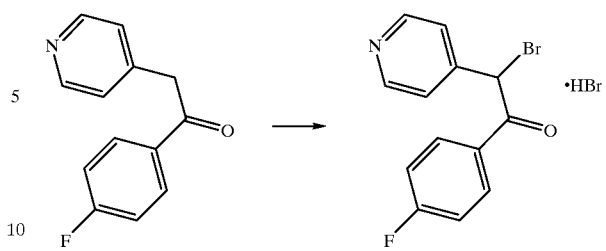

Bromine (74.4 g; 0.46 mol) in acetic acid (160 ml) is added within 10 min to a solution of 4-fluorophenyl 4-pyridylmethylketone (I. Lantos et al. J. Med. Chem. 1984, 27, 72–75) (100 g; 0.46 mol) in acetic acid (800 ml) at 21° C. The yellow crystals are filtered off, washed with acetic acid, ether and hexane and then dried under reduced pressure to provide the hydrobromide of the desired compound (250 g; 72%).

b) 4-(4-Fluorophenyl)-2-(1-N-carbobenzyloxycyclohexyl)-5-(4-pyridyl)imidazole

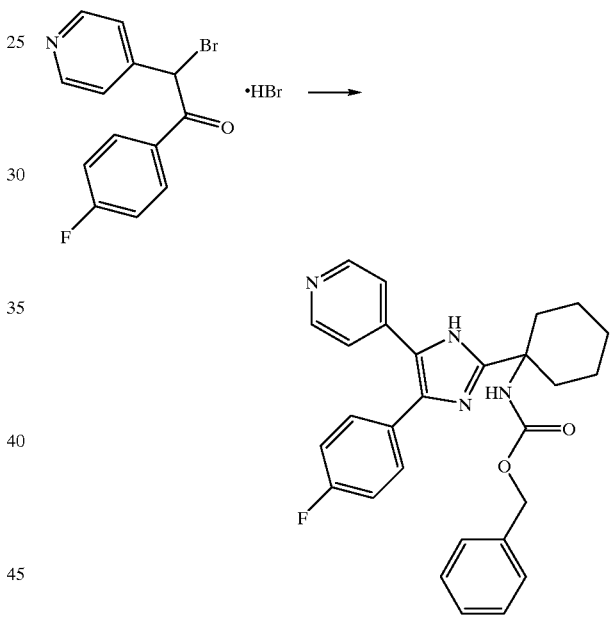

1-N-carbobenzyloxy-1-cyclohexanecarboxylic acid (E. Didier et al. Tetrahedron 1992. 48(39), 8471) (13.9 g; 50 mmol), and ammoniumcarbonate (Fluka; 4.8 g; 50 mmol) are dissolved in DMF (50 ml) and heated to 110° C. for 10 min. until gas evolution ceases. The reaction flask is cooled to 60° C., 1-(4-fluorophenyl)-2-bromo-2-(4-pyridyl) ethanone hydrobromide (3.75 g; 10 mmol) added as a solid and heated to 125° C. for 2.5 h. The reaction mixture is poured on 1M Na₂CO₃ and extracted with ethyl acetate three times. The combined organic phases are washed with water. dried over Na₂SO₄, evaporated to dryness and yielded the crude title compound, (4.8 g) which after chromatography (SiO₂; ethyl acetate) gives the pure title compound as light yellow crystals (1.4 g; 30%).

1H-NMR (400 MHz; CDCl3): 1.25–2.40 (m, 10H); 5.12 (s, 2H); 7.08–7.16 (m, 2H); 7.30–7.50 (m, 9H); 8.50 (d, 2H) MS (m/z): 471.2 (MH+)

c) 4-(4-Fluorophenyl)-2-(1-aminocyclohexyl)-5-(4-pyridyl) imidazole (243–653)

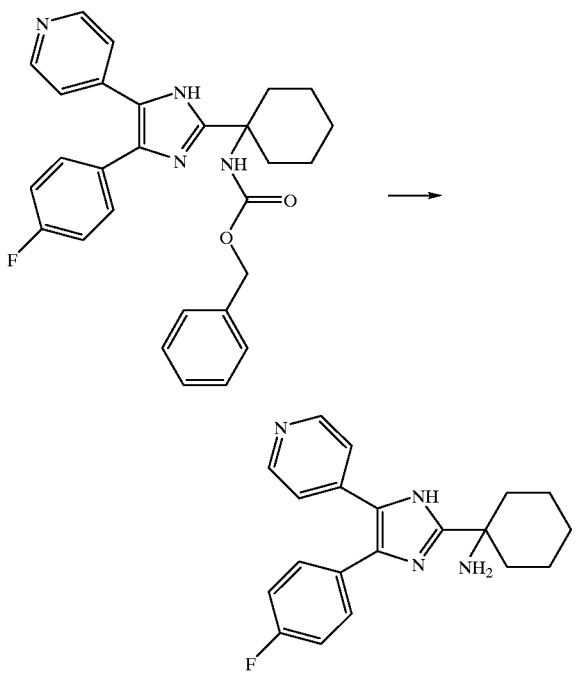

4-(4-Fluorophenyl)-2-((1-N-carbobenzyloxy)cyclohexyl)-5-(4-pyridyl)imidazole (1.6 g; 4 mmol) is dissolved in EtOH (140 ml) and hydrogenated at 1 atm in the presence of Pd/C (10%; 0.7 g) for 2 h at room temperature. Filtration and evaporation of the solvent followed by recrystallisation from ethyl acetate/ether yields the desired amine as off-white crystals (0.63 g; 471%).

1H-NMR (400 MHz; DMSO-d6): 1.25–1.78 (m, 8H); 1.95–2.10 (bt, 2H); 7.25–7.34 (bt, 2H); 7.40 (d, 2H); 7.47–7.5) (m, 2H); 8.43 (d, 2H) MS (m/z): 336 (M+).

Example 19

4-(4-Fluorophenyl)-5-(4-pyridyl) 2-(4-n-butyloxy-1-methylpiperidin-4-yl)imidazole

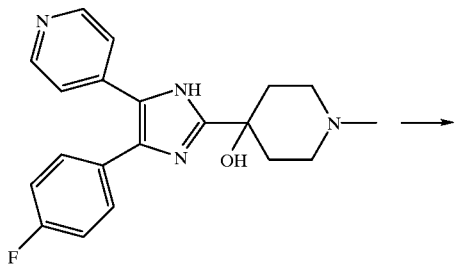

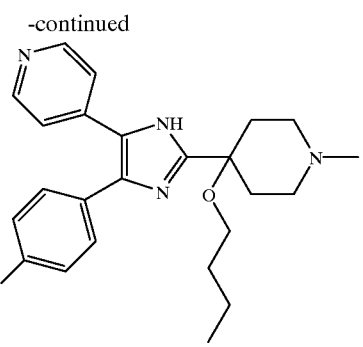

The product of example 12, 4-(4-Fluorophenyl)-5-(4-pyridyl) 2-(4-hydroxy-1-methylpiperidin-4-yl)imidazole (22.2 g; 63 mmol) is dissolved in 1-butanol (1 l) upon warming to 40° C. $H_2SO_4$ conc (27.8 g; 283 mmol) is added dropwise and the initially resulting suspension is refluxed for 3.5 h, while distilling off ~200 ml of 1-butanol. The reaction mixture is cooled to room temperature and poured on a saturated solution of $Na_2CO_3$ (500 ml). The aqueous phase is extracted with ethyl acetate and the combined organic phases dried over $Na_2SO_4$, filtered and evaporated to dryness. Purification by chromatography ($SiO_2$; TBME/MeOH/$NH_3$conc. 96/4/0.4 to 70/30/1) yields the title compound as yellow crystals (15.5 g; 60.3%). A sample is recrystallized from $CH_2Cl_2$/TBME to render colorless crystals: m.p. 177° C.

1H-NMR (400 MHz; DMSO-d6): mixture of tautomers, which duplicates aromatic signals. 0.80 (bt, 3H); 1.25–1.35 (m, 2H); 1.38–1.48 (m, 2H); 2.12 (bs, 4H); 2.18 (s, 3H); 2.35 (m, 2H); 2.42 (m, 2H); 3.12 (t, 2H); 7.18 (t, 0.5H); 7.32 (t, 1.5H); 7.40 (m, 2H); 7.48 (m, 2H); 8.40 (d, 1.5H); 8.53 (d, 0.5H). MS (m/z): 408 (M+, 20%); 351 (100%); 335 (95%).

Compounds of the Invention. in free or pharmaceutically acceptable acid addition salt or physiologically cleavable ester form, which exhibit pharmacological activity and are useful as pharmaceuticals, e.g. for therapy, in the treatment of diseases and conditions as hereinafter set forth, are hereinafter referred to as Agents of the Invention.

In particular Agents of the Invention possess p38 MAP kinase (Mitogen Activated Protein Kinase) inhibiting activity. Thus the Agents of the Invention act to inhibit production of inflammatory cytokines, such as TNF-α and IL-1, and also to potentially block the effects of these cytokines on their taret cells. These and other pharmacological activities of the Agents of the Invention as may be demonstrated in standard test methods for example as described below:

p38 MAP kinase Assay

The substrate (GST-ATF-2; a fusion protein comprising amino acids 1–109 of ATF-2 and the GST protein obtained by expression in *E. coli*) is coated onto the wells of microtiter plates (50 μl/well; 1 μg/ml in PBS/0.02% Na azide) overnight at 4° C. The following day, the microtiter plates are washed four times with PBS/0.5% Tween 20/0.02% Na azide and are blocked with PBS/2% BSA/0.02% Na Azide for 1 h at 37° C. Plates are washed again 4 times with PBS/0.5% Tween 20/0.02% Na azide. The kinase cascade reaction is then started by adding the following reactants in 10 μl aliquots to a final reaction volume of 50 μl.

1. Agents of the Invention titrated from 10 to 0.001 μM in 10-fold dilutions or solvent (DMSO) or $H_2O$.

2. Kinase buffer (5×); pH 7.4; 125 mM Hepes (Stock at 1M; Gibco #15630-056). 125 mM β-glycerophosphate (Sigma #G-6251): 125 mM MgCl$_2$ (Merck #5833); 0.5 mM Sodium orthovanadate (Sigma #5-6508), 10 mM DTT (Boehringer Mannheim #708992). The (5×) kinase buffer must be prepared fresh the day of the assay from 5× stock solutions kept at RT. DTT is kept at −20° C. and is added as the last reagent.
3. His-p38 MAP kinase (10 ng/well; Novartis—a fusion protein comprising full length murine p38 MAP kinase and a His tag, obtained by expression in *E. coli*)
4. cold ATP (final concentration 120 μM: Sigma #A-9187)
5. Water After 1 h at 37° C. the kinase reaction is terminated by washing the plates four times as previously described. Phosphorylated GST-ATF-2 is then detected by adding:
1. the PhosphoPlus ATF-2 (Thr71) Antibody (50 μl/well; 1/1000 final dilution in PBS/2% BSA/0.02% Na Azide; New Enaland Biolabs #9221L) for 90 min at RT.
2. Biotin labelled goat-anti-rabbit IgG (50 μl/well; 1/3000 final dilution in PBS/2% BSA/0.02% Na Azide; Sigma #B-9642) for 90 min at RT.
3. Streptavidin-alkaline phosphatase (50 μl/well; 1/5000 dilution in PBS/2% BSA/0.02% Na Azide; Jackson Immunoresearch #016-050-084 ) for 30 min at RT.
4. Substrate (100 μl/well; Sigma 104 Phosphatase substrate tablets, 5 mg/tablet; #104–105; 1 mg/ml in substrate buffer, Diethanolamine (97 ml/l Merck #803116)+MgCl$_2$.6H$_2$O (100 mg/l; Merck #5833)+Na Azide (0.2 g/l)+HCl 1M to pH 9.8) 30 min at RT.

After step 1,2 and 3 the microtiter plates are washed four times with PBS/0.5% Tween 20/0.02% Na azide. After step 4, the plates are read in a Bio-Rad microplate reader in a dual wavelength mode (measurement filter 405 nm and reference filter 490 nm). The background value (without ATP) is subtracted and IC$_{50}$ values are calculated using the Origin computer program (4 parameter logistic function).

Agents of the Invention typically have IC$_{50}$s for p38 MAP kinase inhibition in the range from about 1 μM to about 10 nM or less when tested in the above assay. For example, the compound of Example 17 has an IC$_{50}$ of about 10 nM in this assay.

Assay for Inhibition of TNF-α release from hPBMCs

Human peripheral blood mononuclear cells (hPBMCs) are prepared from the peripheral blood of healthy volunteers using ficoll-hypaque density separation accordinc to the method of Hansel et al., J. Imm. Methods (1991) 145: 105, and used at a concentration of $10^5$ cells/well in RPMI 1640 plus 10% FCS. Cells are incubated with serial dilutions of the test compounds for 30 minutes at 37° C. prior to the addition of IFNg (100 U/ml) and LPS (5 mg/ml) and subsequently further incubated for three hours. Incubation is terminated by centrifugation at 1400 RPM for 10 min. TNF-α in the supernatant is measured using a commercial ELISA (Innotest hTNFa, available from Innogenetics N.V., Zwijnaarde, Belium). Agents of the Invention are tested at concentrations of from 0 to 10 mM. Exemplified Agents of the Ivention typically suppress TNF release in this assay with an IC$_{50}$ of from about 1 μM to about 10 nM or less when tested in this assay. For example, the compound of Example 17 has an IC$_{50}$ of about 90 nM when tested in this assay.

Assay for Inhibition of TNF-α Production in LPS Stimulated Mice

Injection of lipopolysaccharide (LPS) induces a rapid release of soluble tumour necrosis factor (TNF-α) into the periphery. This model is be used to analyse prospective blockers of TNF release in vivo.

LPS (20 mg/kg) is injected i.v. into OF1 mice (female, 8 week old). One (1) hour later blood is withdrawn from the animals and TNF levels are analysed in the plasma by an ELISA method using an antibody to TNF-α. Using 20 mg/kg of LPS levels of up to 15 ng of TNF-α/ml plasma are usually induced. Compounds to be evaluated are given either orally or s.c. 1 to 4 hours prior to the LPS injection. Inhibition of LPS-induced TNF-release is taken as the readout.

Agents of the Invention typically inhibit TNF production to the extent of from about 50% up to about 90% or more in the above assay when administered at 10 mg/ka p.o. For example the compound of Example 17 inhibits TNF production to the extent of about 80% in this assay.

As indicated in the above assays Agents of the Invention are potent inhibitors of TNF-α release. Accordingly, the Novel Compounds have pharmaceutical utility as follows:

Agents of the Invention are useful for the prophylaxis and treatment of diseases or pathological conditions mediated by cytokines such as TNFα and IL-1, e.g. inflammatory conditions, autoimmune diseases, severe infections. and organ or tissue transplant rejection, e.g. for the treatment of recipients of heart, lung, combined heart-lung, liver, kidney, pancreatic, skin or corneal transplants and for the prevention of graft-versus-host disease, such as following bone marrow transplants.

Agents of the Invention are particularly useFul for the treatment, prevention, or amelioration of autoimmune disease and of inflammatory conditions, in particular inflammatory conditions with an aetiology including an autoimmune component such as arthritis (for example rheumatoid arthritis, arthritis chronica progrediente and arthritis deformans) and rheumatic diseases. Specific auto-immune diseases for which Agents of the Invention may be employed include autoimmune haematological disorders (including e.g. hemolytic anaemia, aplastic anaemia, pure red cell anaemia and idiopathic thrombocytopenia), systemic lupus erythematosus, polychondritis, sclerodoma, Wegener granulamatosis, dermatomyositis, chronic active hepatitis, myasthenia gravis, psoriasis, Steven-Johnson syndrome, idiopathic sprue, autoimmune inflammatory bowel disease (including e.g. ulcerative colitis and Crohn's disease), endocrine ophthalmopathy, Graves disease, sarcoidosis, multiple sclerosis, primary biliary cirrhosis, juvenile diabetes (diabetes mellitus type I), uveitis (anterior and posterior), keratoconjunctivitis sicca and vernal keratoconjunctivitis, interstitial lung fibrosis, psoriatic arthritis and glomerulonephritis (with and without nephrotic syndrome, e.g. including idiopathic nephrotic syndrome or minimal change nephropathy).

Agents of the Invention are also useful for the treatment, prevention, or amelioration of asthma, bronchitis, pneumoconiosis, pulmonary emphysema, and other obstructive or inflammatory diseases of the airways.

Agents of the Invention are useful for treating undesirable acute and hyperacute inflammatory reactions which are mediated by TNF, especially by TNFa, e.g., acute infections, tor example septic shock (e.g., endotoxic shock and adult respiratory distress syndrome), meningitis, pneumonia; and severe burns; and for the treatment of cachexia or wasting syndrome associated with morbid TNF release, consequent to infection, cancer, or organ dysfunction, especially AIDS-related cachexia, e.g., associated with or consequential to HIV infection.

Agents of the Invention are particularly useful for treating diseases of bone metabolism including osteoarthritis, osteoporosis and other inflammatory arthritides.

For the above indications the appropriate dosage will, of course, vary depending, for example, on the particular Agent of the Invention employed, the subject to be treated, the mode of administration and the nature and severity of the condition being treated. However, in general, satisfactory results in animals are obtained at daily dosages of from about 1 to about 10 mg/kg/day p.o. In larger mammals, for example humans, an indicated daily dosage is in the range of from about 50 to about 750 mg of Agent of the Invention administered orally once or, more suitably, in divided dosages two to four times/day.

The Agents of the Invention may be administered by any conventional route, e.g. orally, for example in the form of solutions for drinking, tablets or capsules or parenterally, for example in the form of injectable solutions or suspensions. Normally or systemic administration oral dosage forms are preferred, although for some indications the Agents of the Invention may also be administered topically or dermally, e.g. in the form of a dermal cream or gel or like preparation or, for the purposes of application to the eye, in the form of an ocular cream, gel or eye-drop preparation; or may be administered by inhalation, e.g., for treating asthma. Suitable unit dosage forms for oral adhinistration comprise e.g. from 25 to 250 mg Novel Compound per unit dosage.

In accordance with the foregoing the present invention also provides in a further series of embodiments:

A. A method of inhibiting production of soluble TNF, especially TNFα, or of reducing, inflammation in a subject i.e., a mammal, especially a human) in need of such treatment which method comprises administering to said subject an effective amount of an Agent of the Invention, or a method of treating any of the above mentioned conditions, particularly a method of treating an inflammatory or autoimmune disease or condition, e.g. rheumatoid arthritis, or alleviating one or more symptoms of any of the above mentioned conditions.

B. An Agent of the Invention for use as a pharmaceutical, e.g. for use as an immunosuppressant or antuinflammatory agent or for use in the prevention, amelioration or treatment of any disease or condition as described above, e.g., an autoimmune or inflammatory disease or condition.

C. A pharmaceutical composition comprising an Agent of the Invention in association with a pharmaceutically acceptable diluent or carrier, e.g., for use as an immunosuppressant or anti-inflammatory agent or for use in the prevention, amelioration or treatment of any disease or condition as described above, e.g., an autoimmune or inflammatory disease or condition.

D. Use of an Agent of the Invention in the manufacture of a medicament for use as an immunosuppressant or anti-inflammatory agent or for use in the prevention, amelioration or treatment of any disease or condition as described above, e.g., an autoimmune of inflammatory disease or condition.

What is claimed is:

1. A compound of formnula I

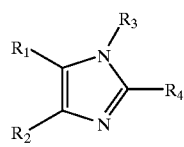

I wherein $R_1$ is 4pyridyl which is optionally substituted with one or two substituents each of which is independently selected from $C_{1-4}$ alkyl, halogen, $C_{1-4}$ alkoxy, $C_{1-4}$ alkylthio and $NR_5R_6$ where $R_5$ and $R_6$ are each independently $C_{1-4}$ alkyl;

$R_2$ is phenyl, naphth-1-yl or naphth-2-yl which is optionally substituted by up to five substituents;

$R_3$ is hydrogen; and, $R_4$ is optionally substituted pyridyl; in free or pharmaceutically acceptable acid addition salt or physiologically cleavable ester form, provided that $R_2$ is not phenyl substituted with a radical selected from alkylsulfonyl or aminosulfonyl.

2. A compound according to claim 1 selected from:

4-(4-Fluorophenyl)-5-(4pyridyl) 2-(2,3,5,6-tetrafluoropyridinyl)imidazole;

4-(4-Fluorophenyl)-5-(4pyridyl) 2-(2-amino-3,5,6-trifluoropyridinyl)imidazole;

4-(4-Fluorophenyl)-5-(4pyridyl) 2-(2,6-diamino-3,5-difluoropyridinyl)imidazole.

3. A method of inhibiting production of soluble TNF or of reducing inflammation in a subject in need of such treatment which method comprises administering to said subject an effective amount of a compound according to claim 1.

4. A pharmaceutical composition comprising a compound according to claim 1 in association with a pharmaceutically acceptable diluent or carrier.

5. A process for the preparation of a compound of formulae I as defined in claim 1 comprising reacting a compound of formula VIII

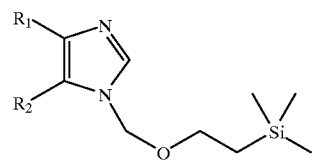

VIII wherein $R_1$ and $R_2$ are as defined in claim 1, with the corresponding aldehyde, ketone, disuffonylamine, disulfide, diselenide, ditelluride or halide and, if required, further transforming the product obtained and optionally recovering the compound in free or salt form.

6. A method of treatment of an inflammatory or autoimmune disease or condition comprising administering to a subject in need of such treatment an effective amount of a compound according to claim 1.

7. A method of treatment of rheumatoid arthritis comprising administering to a subject in need of such treatment an effective amount of a compound according to claim 1.

* * * * *